(12) United States Patent
Conchy et al.

(10) Patent No.: US 6,749,612 B1
(45) Date of Patent: Jun. 15, 2004

(54) SPINAL OSTEOSYNTHESIS SYSTEM WITH IMPROVED RIGIDITY

(75) Inventors: Frédéric Conchy, Saint-Médard-d'Eyrans (FR); Richard Assaker, Kain (BE)

(73) Assignee: Stryker Spine (FR)

( * ) Notice: Subject to any disclaimer, the term of this patent is extended or adjusted under 35 U.S.C. 154(b) by 0 days.

(21) Appl. No.: 09/807,092

(22) PCT Filed: Oct. 7, 1999

(86) PCT No.: PCT/FR99/02402
§ 371 (c)(1),
(2), (4) Date: Jul. 11, 2001

(87) PCT Pub. No.: WO00/21447
PCT Pub. Date: Apr. 20, 2000

(30) Foreign Application Priority Data

Oct. 9, 1998 (FR) .............................................. 98 12662

(51) Int. Cl.[7] .......................... A61B 17/56; A61B 17/58; A61F 2/30
(52) U.S. Cl. ....................................................... 606/61
(58) Field of Search .............................. 606/60, 61, 72, 606/73; 623/17

(56) References Cited

U.S. PATENT DOCUMENTS

| | | | |
|---|---|---|---|
| 4,289,123 A | 9/1981 | Dunn | |
| 4,987,892 A | 1/1991 | Krag et al. | |
| 5,108,395 A | 4/1992 | Laurain | |
| 5,147,360 A | 9/1992 | Dubousset | |
| 5,236,460 A | 8/1993 | Barber | |
| 5,380,324 A | 1/1995 | Muller et al. | |
| 5,609,635 A | 3/1997 | Michelson | |
| 5,620,443 A * | 4/1997 | Gertzbein et al. ............ | 606/61 |
| 5,628,740 A | 5/1997 | Mullane | |
| 5,662,652 A | 9/1997 | Schäfer et al. | |
| 5,683,391 A | 11/1997 | Boyd | |
| 5,702,395 A * | 12/1997 | Hopf ............................ | 606/61 |
| 5,713,898 A | 2/1998 | Stücker et al. | |
| 5,800,550 A | 9/1998 | Sertich | |
| 5,938,663 A | 8/1999 | Petreto | |
| 6,004,322 A | 12/1999 | Bernstein | |
| 6,123,706 A | 9/2000 | Lange | |
| 6,132,431 A | 10/2000 | Nilsson et al. | |
| 6,146,383 A * | 11/2000 | Studer et al. ................ | 606/61 |
| 6,299,614 B1 | 10/2001 | Kretschmer et al. | |
| 6,328,739 B1 | 12/2001 | Liu et al. | |
| 6,423,064 B1 | 7/2002 | Kluger | |

FOREIGN PATENT DOCUMENTS

| | | | | |
|---|---|---|---|---|
| DE | 94 12 744 U | 1/1996 | | |
| DE | 4433360 A1 * | 2/1996 | ................ | 606/61 |
| DE | 195 34 136 A1 | 3/1996 | | |
| DE | 297 12 697 U1 | 11/1997 | | |
| EP | 0 697 200 A1 | 2/1996 | | |
| EP | 0 726 064 A2 | 8/1996 | | |
| FR | 2 244 446 | 4/1975 | | |
| FR | 2 697 744 | 5/1994 | | |
| FR | 2 730 159 A1 | 8/1996 | | |
| WO | WO 93/20771 * | 10/1993 | ................ | 606/61 |
| WO | WO 94/06360 | 3/1994 | | |
| WO | WO 96/27340 | 9/1996 | | |
| WO | WO 00/01314 | 1/2000 | | |

* cited by examiner

*Primary Examiner*—Tuan N. Nguyen
(74) *Attorney, Agent, or Firm*—Lerner, David, Littenberg, Krumholz & Mentlik, LLP

(57) ABSTRACT

A spinal osteosynthesis system, in particular for anterior spinal fixation, comprising at least an anchoring member, an elongated linking element and a connector capable of being fixed to the anchoring member and to the linking element by selecting an angular position of the linking element relative to the connector. The system comprises a second elongated linking element, the connector being capable of being fixed simultaneously to both linking elements.

21 Claims, 5 Drawing Sheets

FIG_1

SPINAL OSTEOSYNTHESIS SYSTEM WITH IMPROVED RIGIDITY

CROSS-REFERENCE TO RELATED APPLICATIONS

This application is a National Stage of International Application No. PCT/FR99/02402, filed Oct. 7, 1999, the disclosure of which is hereby incorporated by reference herein.

BACKGROUND OF THE INVENTION

The invention relates to spinal osteosynthesis systems, in particular for anterior fixation.

Spinal osteosynthesis systems for anterior fixation are known in which the connection element is formed by a plate, and others are known in which the connection element is formed by a rod. Because of their bulk, the plate systems are difficult to use, if they can be used at all, via the endoscopic route. Moreover, their limited size (length) means that they can only be used for simple vertebrectomies involving a single vertebra, or perhaps two. It is impossible to treat scoliosis with this type of system. Finally, a plate is difficult to adapt to the morphology of the vertebrae in which it is anchored. Moreover, the rod systems generally comprise fairly voluminous connectors which cannot always be used via the endoscopic route.

A spinal osteosynthesis device is also known from U.S. Pat. No. 5,938,663, which device comprises a clamp or connector with two branches which can clamp a connection rod between them, the branches being able to be engaged on a vertebral pedicle screw. The rod is received between the branches with interposition of a slotted ring which has a spherical face and is engaged on the rod in order to control the angular orientation of the connector relative to the rod before clamping. However, this device, while well suited for posterior fixation of the spine on the vertebral pedicles, does not always provide sufficient rigidity with a view to anterior fixation of the spine.

SUMMARY OF THE INVENTION

An object of the invention is to make available a different spinal osteosynthesis system, adapted for anterior fixation, easy to fit, ensuring good rigidity of the system on the spine, and compatible with being fitted via the endoscopic route.

To achieve this object, the invention provides a spinal osteosynthesis system, in particular for anterior fixation, comprising at least one anchoring member, an elongate connection element and a connector which is able to be fixed to the anchoring member and to the connection element by choosing an angular position of the connection element relative to the connector, the system comprising a second elongate connection element, the connector being able to be fixed simultaneously to the two connection elements.

Thus, the presence of the two connection elements gives the system very great rigidity, without complicating its assembly, without increasing the volume of its various components (which renders it compatible with fitting via the endoscopic route), and while maintaining the possibility of controlling the angular position of the connector relative to the first connection element. The system according to the invention does not require identical bending on the two connection elements. Moreover, the number of connectors can remain small.

Advantageously, the system is designed in such a way that the second connection element can be fixed to the connector only in a single angular position relative to the connector.

Thus, the shape of the second connection element dictates the relative angular position of the connectors which are fixed to it. This angular position can therefore be chosen in advance depending on the prior curvature given to this connection element, either at the time of manufacture or, better still, during the surgical intervention.

Advantageously, the second connection element has less resistance to bending than the first connection element.

Thus, the first connection element has mainly a function ensuring support of the connectors, and the second connection element has mainly a function ensuring angular positioning of the connectors.

Advantageously, the connector comprises two branches which can clamp at least one of the two connection elements.

Advantageously, the branches have first ends via which they are connected to each other and second free ends.

This simplifies production of the connector. Moreover, by appropriately selecting the flexibility of the connector and/or the diameter of the second connection element, this element can be introduced laterally between the free ends of the branches, which makes fitting easier.

Advantageously, the connector is able to receive the second connection element by lateral insertion between the free ends.

Advantageously, the branches can simultaneously clamp the two connection elements.

Advantageously, the anchoring member comprises a vertebral screw, at least a first of the two branches being able to be engaged on the screw.

Advantageously, the vertebral screw has a threaded orifice, the system comprising a clamping screw which can constitute a screw-nut connection with this orifice and is able to bear on one of the branches in order to clamp the branches.

Advantageously, the system comprises a second vertebral screw, the first branch being able to be engaged simultaneously on the two vertebral screws.

Advantageously, the system is designed in such a way that the second connection element, when fixed to the connector, extends in a trajectory of the second vertebral screw for its disengagement from the connector.

Thus, the second screw is prevented from starting to come out at an inopportune moment.

Advantageously, the system comprises a ring which can be engaged on the first connection element and received between the branches in order to choose the angular position of the first connection element before the branches are clamped.

BRIEF DESCRIPTION OF THE DRAWINGS

Other characteristics and advantages of the invention will become more apparent from the following description of a preferred embodiment given as a nonlimiting example. In the attached drawings.

DETAILED DESCRIPTION OF THE PREFERRED EMBODIMENTS

Figure 1:
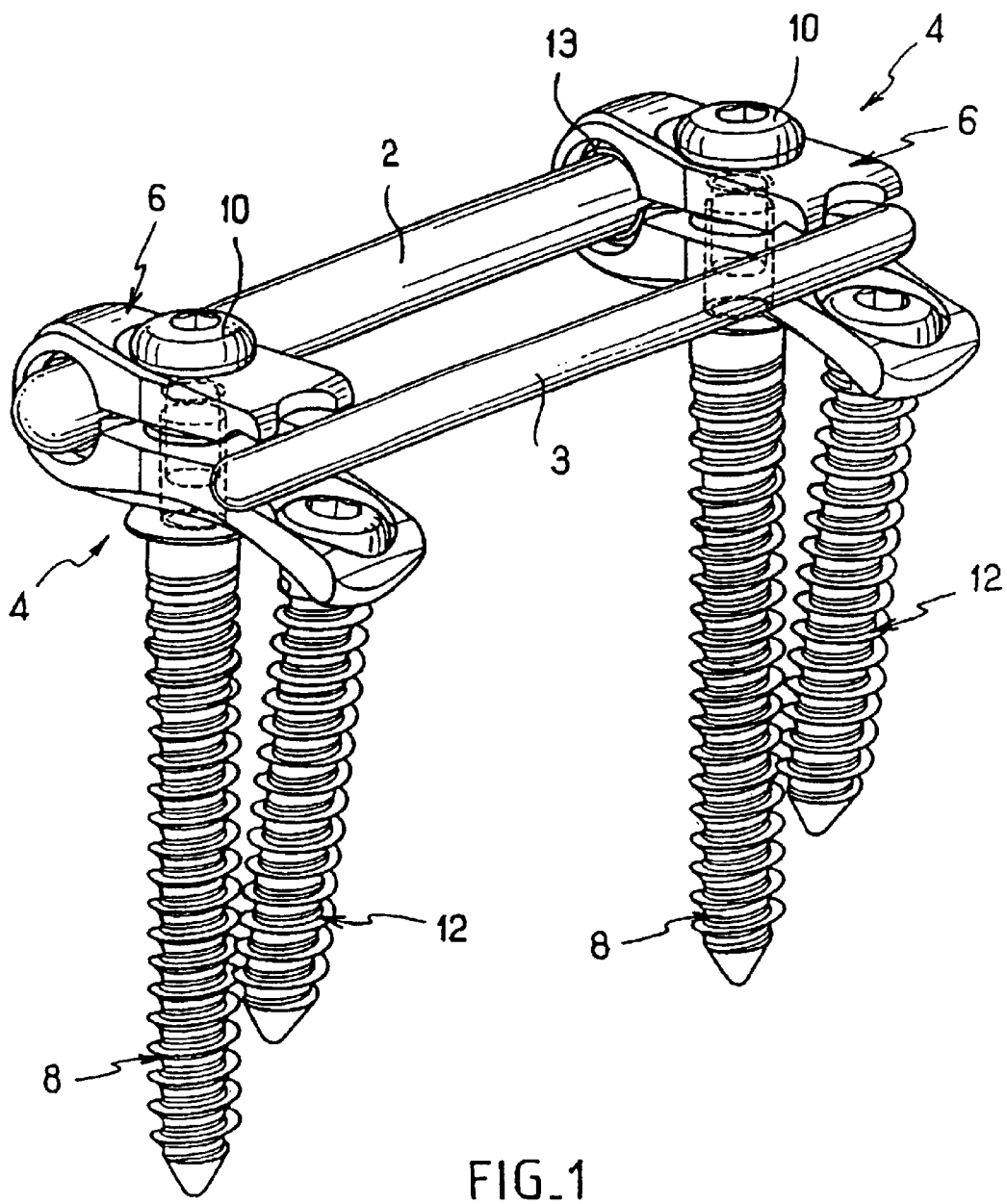
FIG. 1 is a perspective view of the system according to the invention.
Figure 2:
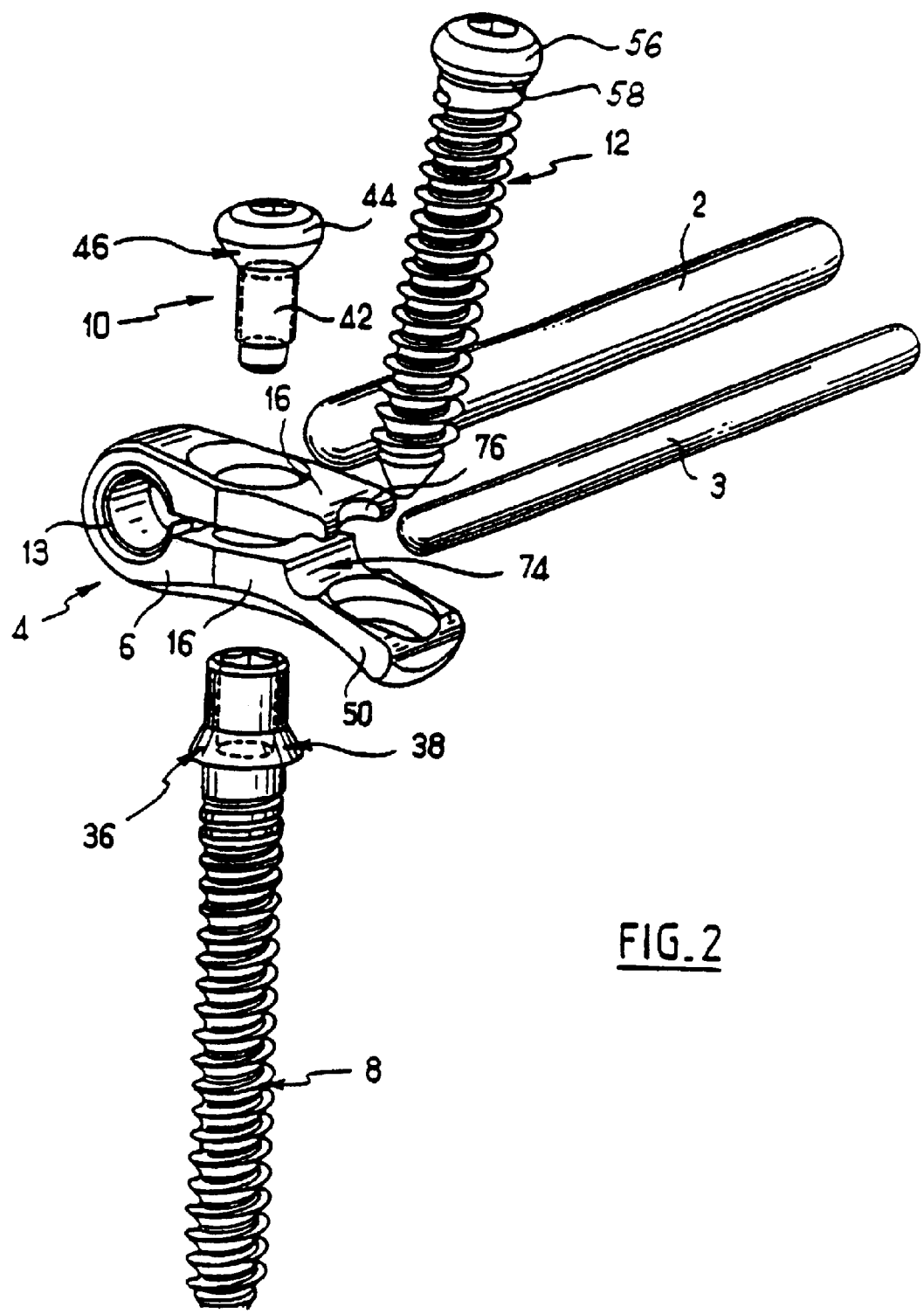
FIG. 2 is a partial and exploded perspective view of the system in FIG. 1.

Referring to FIGS. 1 and 2, the system according to the invention comprises, in the preferred embodiment, a first elongate connection rod 2, or main rod, of circular cross section, a second elongate connection rod 3 or secondary rod of circular cross section and several connector sub-assemblies 4 which can be fixed simultaneously to the latter. Each of these sub-assemblies, of which only two can be seen in FIG. 1 and of which only one can be seen in FIG. 2, comprises a connector 6, a first vertebral screw or main screw 8, a clamping screw 10, a second vertebral screw or secondary screw 12, and a ring 13.

In the present example, the connector 6 is made in one piece. The different parts of the system are made of biocompatible metal.

Figure 3:
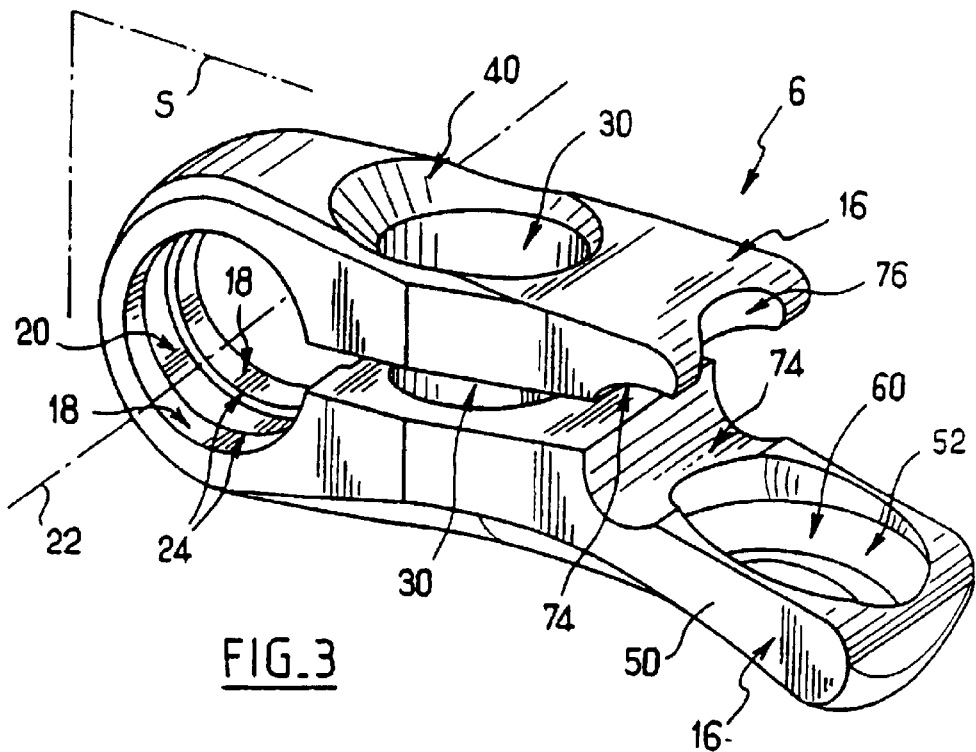
FIGS. 3 and 4 are two perspective views, from above and below, respectively, showing one of the connectors of the system in FIG. 1.
Figure 4:
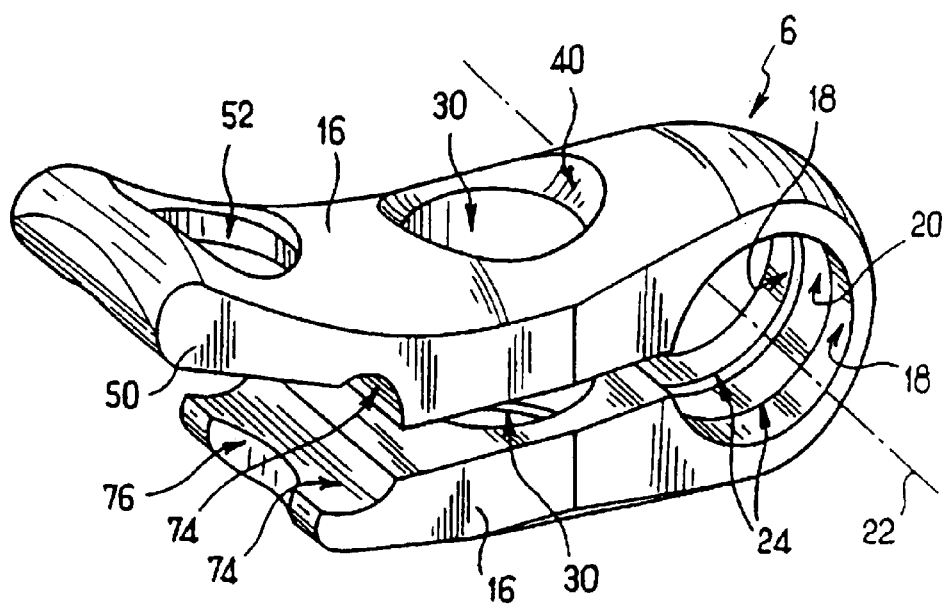

Referring to FIGS. 3 and 4, the preferred connector 6 includes two branches 16 extending opposite to and at a distance from each other, giving the connector a general U-shaped profile. The connector 6 includes a plane of symmetry S visible in FIGS. 3 and 6, perpendicular to the width of the branches 16 and parallel to their length. Thus, each branch has a first end and a second end. The branches are connected to each other via their first ends. The second ends are free ends Referring to FIG. 6, at the point of origin of the branches 16, that is to say of their first end, the connector has two cylindrical and coaxial inner faces 18, 20 with axis 22 perpendicular to the plane S and with different radii. The face 20 of greater radius is in two distinct parts and extends on either side of the face 18 of lesser radius, which is traversed by the plane S. At their junctions, the two faces 18, 20 form two circular edges 24 with axis 22.

Figure 6:
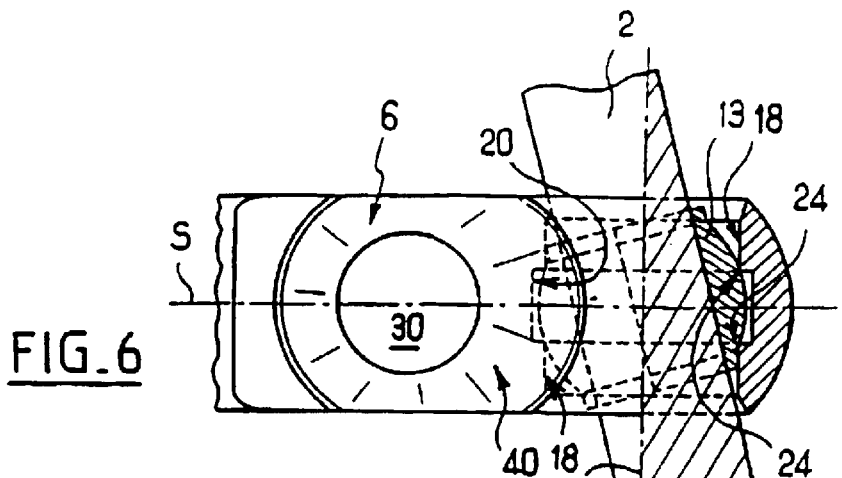
FIG. 6 is a view partly from above and partly in section of the connector in FIG. 3 receiving the first rod.
Figure 5:
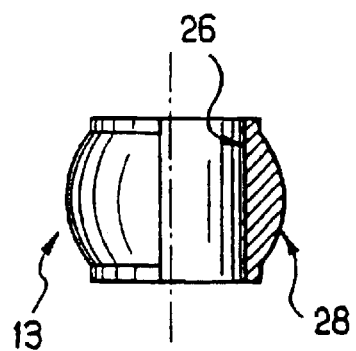
FIG. 5 is a view, half in elevation and half in axial section, of a ring of the system in FIG. 1.

Referring to FIGS. 5 and 6, the preferred ring 13 has a cylindrical inner face 26 and a spherical outer face 28 which are coaxial. The cylindrical inner face 26 has a radius about equal to that of the main rod 2 in such a way that the ring 13, slotted on one side along its axis, can be received as a sliding fit on the main rod 2. Moreover, the ring 13 can be lodged between the branches 16 opposite the cylindrical faces 18, 20. The spherical outer face 28 of the ring has a radius which is adapted such that in this position the edges 24 of the connector 6 are in linear contact with the spherical outer face 28 of the ring 13 and serve as bearings for it. In this position, before clamping of the branches 16, the angular position of the main rod 2 engaged in the ring 13 can be controlled in two mutually perpendicular planes over an amplitude of, for example, 15° on either side of a mean position of the rod in which the rod is perpendicular to the plane S.

Figure 7:
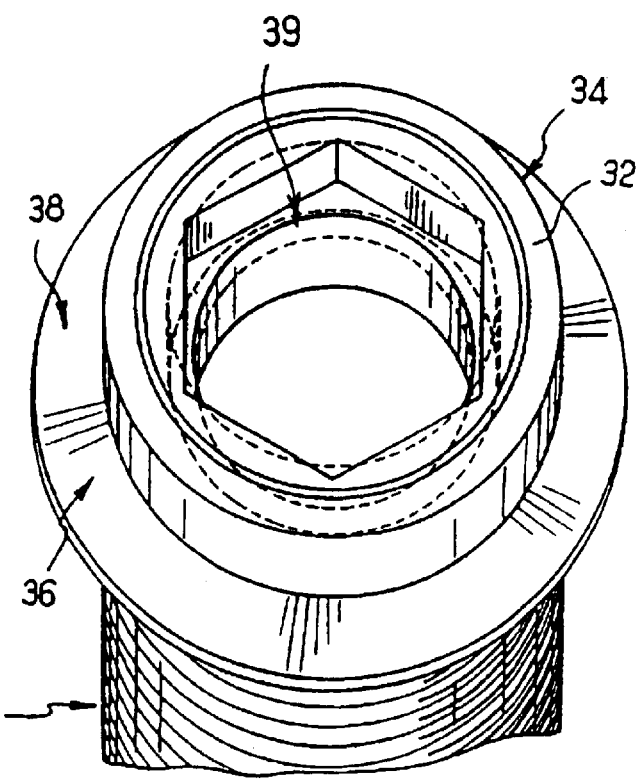
FIG. 7 is a partial perspective view showing the head of the main screw.

Referring to FIGS. 3 and 4, the branches 16 have two respective smooth cylindrical openings which, in this case, are through-orifices 30 extending coaxially opposite each other. The preferred main screw 8 is a bicortical vertebral screw and has a threaded body for this purposes, in a manner known per se. Referring to FIG. 7, it has a head 32 having a smooth cylindrical outer face 34. At the junction between the head and the body, the screw includes an annular flange 36 having a plane lower face perpendicular to a longitudinal axis of the screw, and a frustoconical upper face 38 with the narrowest cross section of the frustum situated towards the head 32 of the screw. The head 32 has a threaded orifice 39 coaxial to the body of the screw and, formed in the threaded face of the orifice 39, a noncircular shape such as a hexagon socket. The clamping screw 10 includes a threaded body 42 which is able to form a screw-nut connection with this orifice 39, and a screw head 44 in which a hexagon socket is formed. The head 44 has a spherical and convex lower outer face 46 whose narrowest cross section is situated towards the point of the screw.

In the preferred embodiment, one of the branches 16 of the connector 6, which for the sake of clarity we will here call the lower branch, has an extension 50 extending in the direction away from the cylindrical faces 18, 20 of the connector. This is the branch intended to be adjacent to the vertebra. This extension has the second, free, end of the branch. The two branches 16 are able to be engaged simultaneously on the head 32 of the main screw 8 introduced in the orifices 30 starting from the lower branch against which the upper face 38 of the flange 36 comes into abutment. The clamping screw 10 is then introduced into the head 32 of the main screw 8 starting from the upper branch 16. The tightening of the clamping screw 10 in the head 32 of the main screw 8 causes the branches 16 to move towards each other and causes, inter alia, frictional blocking of the first rod 2 in the chosen position relative to the connector 6.

The orifice 30 of the lower branch 16 has a lower edge, remote from the upper branch and intended to be towards the vertebra, having a concave spherical recess 40 intended to come into contact with the upper face 38 of the flange 36 in order to effect, by friction, rotational blocking of the connector 6 relative to the axis of the main screw 8. The orifice 30 of the upper branch 16 has an upper edge, remote from the lower branch and intended to be remote from the vertebra, having a concave spherical recess 40 intended to come into contact with the convex and spherical lower face 46 of the head 44 of the clamping screw 10 and making it possible to fix the latter and the main screw 8 by controlling the angular orientation of the main screw 8 relative to the connector.

In the preferred embodiment, the extension 50 has an opening in the form of a through-orifice 52. The lower branch 16 is curved in the area of the extension 50 in a direction away from the upper branch 16 in such a way that the axes of its orifices 30 and 52 are not quite parallel. The secondary screw 12 is a vertebral screw, here a monocortical screw, having a threaded body and a head 56 with a spherical and convex lower face 58 whose narrowest cross section is situated towards the body. Its head has a hexagon socket. The orifice 52 of the extension has an upper edge 60, oriented towards the other branch 16 and intended to be remote from the vertebra, having a spherical and concave or preferably frustoconical form 60, intended to come into contact with the spherical and convex lower face 58 of the head 56 of the secondary screw 12, making it possible to control the angular orientation of this screw relative to the connector 6.

Certain characteristics of the connector 6 which have not been expanded on in detail here will be found in U.S. Pat. No. 5,938,663.

The lower branch 16 can be bent in order to accentuate or reduce its curvature for better adaptation to the shape of the anterior part of the vertebra for which it is intended. Once bent, this branch 16 is no longer stressed in flexion since it is fixed to the vertebra by two screws 8, 12 along its length. The two screws, namely the main screw 8 and the secondary screw 12, are self-tapping and include bone threads.

In an alternative embodiment, the main screw 8 does not have a hexagon socket in this threaded orifice 39, and instead the flange 36 has a hexagonal shape or has two parallel and diametrically opposite flats which can cooperate with a tightening wrench for rotating this screw 8 relative to the connector 6.

The two connection rods 2, 3 each have a profiled rectilinear shape, the profile here being circular. The secondary rod 3 has a cross section, transverse to its longitudinal axis, having a diameter smaller than that of the main rod 2. The main rod 2 will, for example, have a diameter of 6 mm. The diameter of the secondary rod 3 will, for example, be between 30% and 80% of the diameter of the main rod 2. This small diameter allows the surgeon to choose the curvature of the secondary rod 3 corresponding to that of the level of the spine which is being operated on. By contrast, since the rings 13 allow relative angular positioning of the two connectors 6, the main rod 2 does not have to be bent. It can thus have a substantial diameter in order to be very robust.

The branches 16 of the connector have respective cylindrical recesses, grooves or jaws 74 formed in the faces of the branches opposite each other. The recesses 74 extend opposite each other and have axes parallel to each other and perpendicular to the plane of symmetry S.

On the upper branch 16, the recess 74 extends at a free end of the branch such that the orifice 30 is interposed between the faces 18, 20, on the one hand, and the recess 74 on the other. On the lower branch 16, the recess 74 extends between the two orifices 30 and 52, at the origin of the extension 50. It is contiguous with the orifice 52 so that it engages on its edge 60, i.e. recess 74 intercepts the upper opening of orifice 52 as shown in FIG. 3.

The secondary rod 3 is intended to be received in the recess 74 of the lower branch 16 in a unique angular position relative to the connector, perpendicular to the plane of symmetry S. The connector and the rod are dimensioned in such a way that the secondary rod can be introduced laterally between the free ends of the branches (that is to say without engaging the rod via one end in the connector). Before clamping, the space between the branches is wider than the diameter of the rod which can thus be freely inserted. When the two branches 16 are then clamped in the direction of each other, the recess 74 of the upper branch comes into contact with the secondary rod 3 which is thus in surface contact with each of the two recesses, which effect frictional blocking of the secondary rod 3 relative to the connector 6, which are thereby rigidly fixed to each other.

The secondary rod 3 is placed in the recess 74 of the lower branch after the secondary screw 12 has been introduced into the orifice 52. The position of the recess 74 of the lower branch is such that the secondary rod 3 then extends in the trajectory of the head of the secondary screw 12 for its disengagement from the connector and its exit from the orifice 52. Consequently, once the secondary rod 3 has been fixed to the connector, the secondary screw 12 can no longer be separated from the connector.

The upper branch 16 of the connector has at its free end a notch 76 which engages recess 74 with which it is contiguous, and facilitates maneuvering of the clamping screw 12 by means of a tool despite the space occupied by the upper branch.

Figure 8:
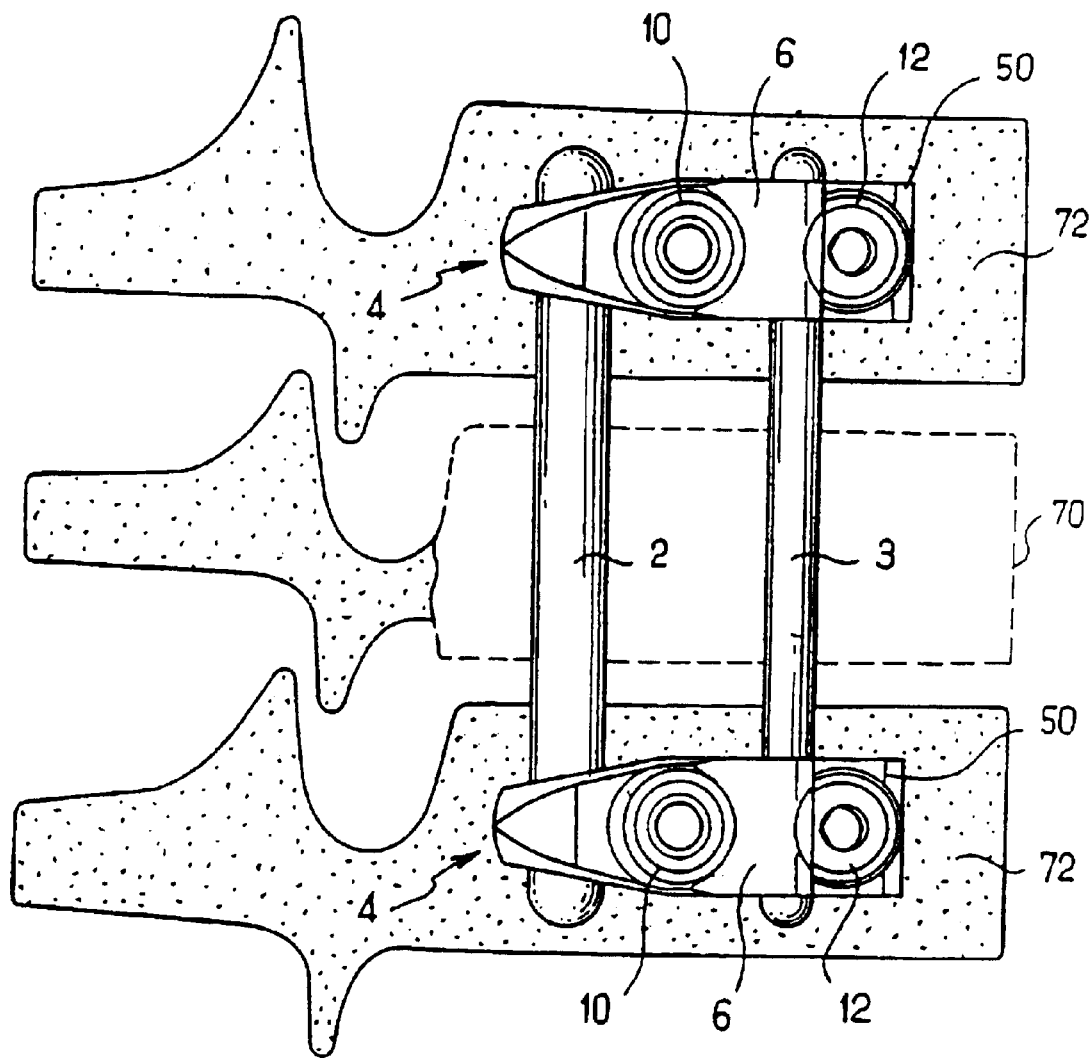
FIG. 8 shows the system from FIG. 1 fixed on vertebrae.

Such a device is fitted in the following manner, with reference to FIG. 8. After exposing the affected vertebra 70 and the two adjacent vertebrae 72, a vertebrectomy is performed while preserving, if possible, the respective plates of these vertebrae. For each subassembly 4, a pilot hole is made on the lateral side of the associated vertebra 72 at an equal distance from the upper and lower plates, and at the limit of the most posterior quarter of the vertebral body. The main screw 8 is then inserted into this pilot hole as far as the limit flange 36. The connector 6 is then positioned on the main screw 8, blocked in translation by the conical face 38 of the main screw 8 matching the recess 40 of the connector 6. The fit of the lower branch 16 of the connector 6 on the vertebra is then checked and can be adjusted by withdrawing the connector in order to bend, to a greater or lesser extent, the lower branch 16, which is its most anterior part.

The secondary screw 12 is then screwed relative to the main screw 8 into the second orifice 52 of the lower branch 16 until the spherical seat 60 of the extension, provided for this purpose, comes into contact with the spherical part 58 of the secondary screw 12. It is desirable to position the connector 6 as parallel as possible to the plates.

After the two adjacent vertebrae 72 have been thus equipped, the main rod 2 is positioned by engaging it via one end in the rings 13 of the connectors 6 and the angular position of each sub-assembly. 4 relative to this rod 2 is controlled. The secondary rod 3 is then introduced laterally, and generally in the medial-lateral direction, into the recesses 74 of the connectors 6 after it has first been bent manually to obtain the curvature required for the corresponding level of the spine. In the event of an error, this rod 3 can be removed laterally in order to correct its curvature and then put back in place. FIG. 1 shows the system before the clamping of the branches. Final clamping is effected by virtue of the clamping screw 10 which is inserted into the main screw 8 and thereby compresses the connector 6 in order to clamp its two branches 16 towards each other. During this clamping, the clamping force is directed first on the main rod 2 via the ring 13, until the recess 74 of the upper branch comes into contact, with the secondary rod 3. Thereafter, the clamping force is distributed on the two rods 2, 3. Thus, the reaction at the level of the pairing of main screw 8 and clamping screw 10 is substantially coaxial to these.

The characteristics relating to the association of the first screw 8 with the clamping screw 10 will be able to be implemented independently of the presence of the extension 50 and of the secondary screw 12.

Although less advantageous, the extended branch can be the one which is intended to be farthest from the vertebra.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A clamp for clamping a pair of rods to the vertebra of the spinal column comprising:

first and second branches each having respective first ends, second ends, and lengths between said first and second ends, said first and second branches being integral at their respective said first ends and free at their respective said second ends, said first and second branches having facing surfaces with rod receiving portions formed thereon for receiving each of said pair of rods therebetween;

at least one bone screw to facilitate attaching said first branch to the vertebra; and a clamping element engaging at least said second branch for clamping said pair of rods within said rod receiving portions of said first and second branches, wherein at least one of said pair of rods is substantially transverse to at least one of said respective lengths of said first and second branches.

2. The clamp of claim 1 wherein said at least one bone screw has a head with a first head portion and a second head portion, said first head portion contacting said vertebra contacting surface of said first branch, said second head portion extending through an opening in said first branch, and said second head portion having an internal threaded portion for cooperative engagement with said clamping element.

3. The clamp of claim 2 wherein said clamping element is a screw having a head engaging said second branch and a threaded portion operatively engaging said internal threaded portion of said second head portion of said at least one bone screw.

4. The clamp of claim 1 wherein said first branch has an opening therein for receiving a second bone screw, said opening intersecting said rod receiving portion on said facing surface on said first branch.

5. The clamp of claim 1 wherein at least one of a first or a second rod of said pair of rods can be fixed to said clamp only in a single angular position relative to said clamp.

6. The clamp of claim 5 wherein said second rod has less resistance to bending than said first rod.

7. The clamp of claim 5 wherein said first and second branches have first ends via which they are connected to one another and second free ends.

8. The clamp of claim 7 wherein said clamp is adapted to receive said second rod via lateral insertion between said second free ends.

9. The clamp of claim 5 wherein said first and second branches are adapted to simultaneously clamp said pair of rods.

10. The clamp of claim 5 wherein said at least one bone screw comprises a first vertebral screw, and at least said first of said first and second branches of said clamp is adapted to be engaged on said first vertebral screw.

11. The clamp of claim 10 wherein said first vertebral screw has a threaded orifice, and wherein said clamping element comprises a clamping screw adapted for threaded engagement with said threaded orifice of said first vertebral screw, and adapted to bear on said second branch of said clamp in order to clamp said two branches together.

12. The clamp of claim 10 wherein said at least one bone screw further comprises a second vertebral screw, and one of said first and second branches of said clamp is adapted to be engaged simultaneously on said first and second vertebral screws.

13. The clamp of claim 12 wherein one of said pair of rods, when fixed to said clamp, extends over a trajectory of said second vertebral screw such that said one of said pair of rods prevents disengagement of said vertebral screw from said clamp.

14. The clamp of claim 1 wherein said pair of rods comprise a first and second rod, and wherein said second rod has less resistance to bending than said first rod.

15. The clamp of claim 1 wherein said first and second branches have first ends via which they are connected to one another and second free ends.

16. The clamp of claim 15 wherein said clamp is able to receive said second rod by lateral insertion between said free ends.

17. The clamp of claim 1 wherein said first and second branches are able to simultaneously clamp said pair of rods.

18. The clamp of claim 1 wherein said at least one bone screw comprises a first vertebral screw, and at least said first of said first and second branches of said clamp is adapted to be engaged on said first vertebral screw.

19. The clamp of claim 18 wherein said first vertebral screw has a threaded orifice, and wherein said clamping element comprises a clamping screw adapted for threaded engagement with said threaded orifice of said first vertebral screw, and is adapted to bear on said second branch of said clamp in order to clamp said two branches together.

20. The clamp of claim 18 wherein said at least one bone screw further comprises a second vertebral screw, and one of said first and second branches of said clamp is adapted to be engaged simultaneously on said first and second vertebral screws.

21. The clamp of claim 20 wherein one of said pair of rods, when fixed to said clamp, extends over a trajectory of said second vertebral screw such that said one of said pair of rods prevents disengagement of said second vertebral screw from said clamp.

* * * * *